(12) United States Patent
Vukovic

(10) Patent No.: US 7,537,671 B2
(45) Date of Patent: May 26, 2009

(54) SELF-CALIBRATING OPTICAL EMISSION SPECTROSCOPY FOR PLASMA MONITORING

(75) Inventor: Mirko Vukovic, Slingerlands, NY (US)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 11/536,976

(22) Filed: Sep. 29, 2006

(65) Prior Publication Data

US 2008/0078504 A1    Apr. 3, 2008

(51) Int. Cl.
  *H01L 21/306*  (2006.01)
  *C23F 1/00*    (2006.01)
  *C23C 16/00*   (2006.01)
(52) U.S. Cl. .............. 156/345.24; 118/712; 118/723 R; 156/345.28
(58) Field of Classification Search .............. 118/723 R
  See application file for complete search history.

(56) References Cited

U.S. PATENT DOCUMENTS 4,837,794 A * 6/1989 Riordan et al. .............. 378/119

2005/0173375 A1 * 8/2005 Mitrovic et al. .............. 216/60
2005/0189069 A1 * 9/2005 Ludviksson et al. ..... 156/345.24

* cited by examiner

*Primary Examiner*—Michael Cleveland
*Assistant Examiner*—Nathan K Ford
(74) *Attorney, Agent, or Firm*—Wood, Herron & Evans, L.L.P.

(57) ABSTRACT

A plasma processing system and plasma monitor therefor is provided in which a plasma monitor housing is coupled to a plasma processing chamber such that a line-of-sight monitoring path extends through the housing to an optical sensor outside of a window. A separate reference signal path extends through the housing from a reference light source on one side of the housing to a reference optical sensor on the other side of the housing. The housing is configured so that deposits from the chamber affect all of the windows equally, and to retard the flow of contaminating film forming material onto the windows, using, for example, baffles, gas counterflow, and a balanced radial-leg housing. A processor uses the reference signal to determine window contamination and compensate for signal attenuation along the monitoring path caused by window coating, in the making of a measurement of plasma emissions. The measurement can be used by the processing system to control the plasma.

12 Claims, 1 Drawing Sheet

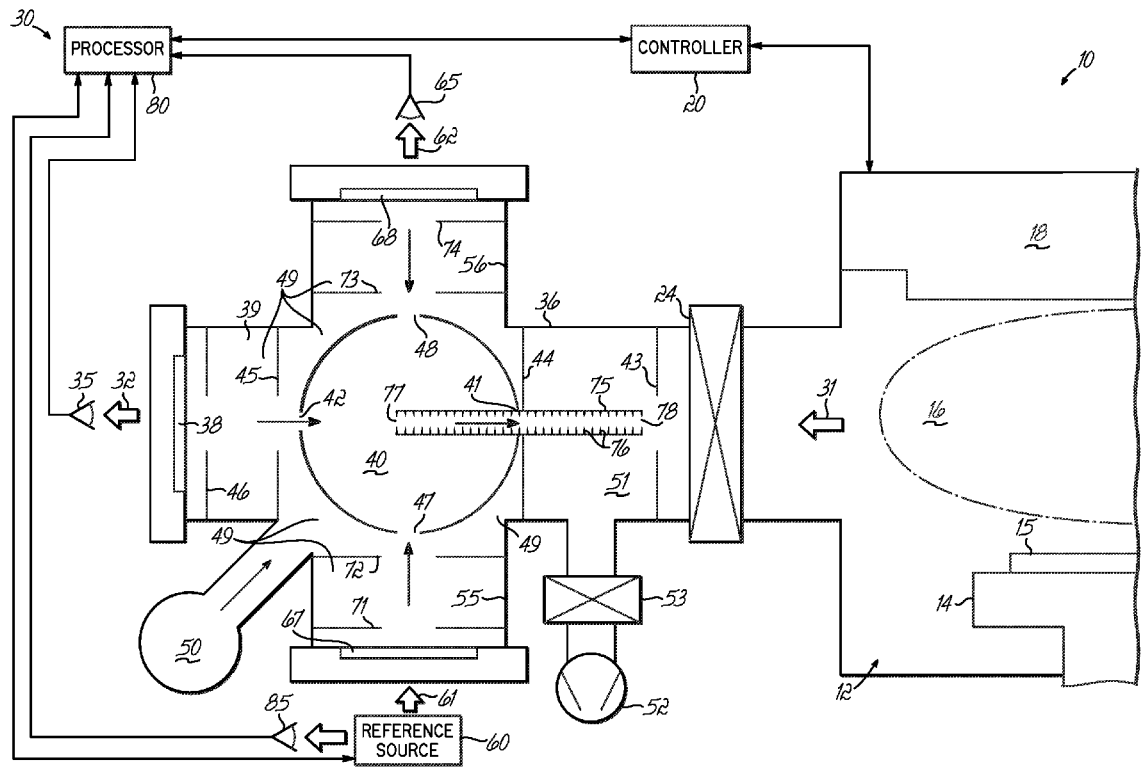

SELF-CALIBRATING OPTICAL EMISSION SPECTROSCOPY FOR PLASMA MONITORING

This application is related to U.S. patent application Ser. No. 11/082,223, filed Mar. 17, 2005, which is a continuation of International Application No. PCT/US03/26208, filed Aug. 21, 2003, which claims priority to U.S. Provisional Application No. 60/414,348, filed Sep. 30, 2002, the contents of all of which are hereby expressly incorporated herein by reference.

This application is also related to U.S. patent application Ser. No. 11/082,246, filed Mar. 17, 2005, and abandoned Mar. 6, 2008, which is a continuation of International Application No. PCT/US03/30051, filed Sep. 25, 2003, which claims priority to U.S. Provisional Application No. 60/414,349, filed Sep. 30, 2002, the contents of all of which are hereby expressly incorporated herein by reference.

FIELD OF INVENTION

This invention relates to plasma processing, and particularly to plasma monitoring of the plasma in vacuum chambers of plasma processing systems.

BACKGROUND OF THE INVENTION

Plasma processes are widely used for applying and etching thin films, particularly in the manufacture of semiconductors where micron and sub-micron thick layers of conductor, semi-conductor and insulator material are deposited, stacked and etched, in repeated cycles. In such manufacture, the properties of the plasma must be carefully controlled to maintain the quality, uniformity and consistency of the processed films. Precise control of the plasmas requires exact knowledge of the state of the plasma being controlled.

Optical methods are widely used to monitor the properties of plasmas and states and courses of plasma processes, particularly in the semiconductor manufacture industry. Observable radiation emitted from a plasma contains much information regarding the nature of the plasma present in a vacuum chamber that can be used by an operator or a programmed controller in the control of the plasma process. For the information to be used, the radiation emitted from the plasma must be accurately measured.

Optical emission spectroscopy is a measurement technique used in plasma processes to measure a full spectrum of radiation emitted from a plasma over a given range of wavelengths, particularly those that include visible and near visible light. This measurement technique involves some optical element such as a transparent lens or window through which spectroscopy sensors can observe the plasma and read emissions from the plasma for measurement and analysis. A light transmissive window is typically used to separate the plasma process chamber from the optical detection system and to allow the spectroscopy equipment to be situated in an ordinary atmosphere environment away from the vacuum environment within the chamber containing the plasma.

In the course of plasma vacuum processes that involve deposition and etching, vapors of various coating materials, reactants, etch byproducts, and other materials tend to fill the vacuum space within the chamber. Eventual deposition of coatings on the view windows through which optical detectors observe the plasma is common. Such deposits affect the window transparency and the radiation being monitored, and can affect the accuracy of the optical measurements if the change in window transparency is not considered.

When the windows through which optical measurements of plasma processes become clouded with film, they can and ultimately must be cleaned or replaced for the plasma process to continue. Such window maintenance involves processing system down-time, which is expensive.

In United States Patent Application 2005/0173375, a related application identified above, an apparatus and method for use of an optical system with a plasma processing system is disclosed. In this published application, the disclosed system and method are provided in conjunction with a plasma processing system, and the system is constructed and arranged to detect a plasma process condition through the window as well as the transmission condition of the window. The method includes detecting an optical emission from the plasma processing region and monitoring contamination of the window through which the plasma is being observed by the optical system.

In addition to the monitoring the contamination of the window through which a plasma is being observed, the simplicity and reliability of the instrumentation, the length of the time between window servicings, and the accuracy and usefulness of the monitored information, affect the quality and efficiency of the plasma process. Accordingly, constant improvement is needed in optical monitoring and control systems for plasma processes, particularly in semiconductor manufacture.

SUMMARY OF THE INVENTION

An objective of the present invention is to improve the simplicity and reliability of the instrumentation, the length of the time between window servicing, and the accuracy and usefulness, of optical emission spectroscopy in the monitoring of plasma processes, particularly those used in the manufacture of semiconductors and other related products.

A more particular objective of the present invention is to provide a method and apparatus for monitoring the conditions of a plasma in a vacuum processing chamber while also determining the condition of the view window through which emissions from the plasma are being measured.

A further objective of the invention is to provide for the calibration or correction of a optical emission spectrographic measurement of plasma conditions and for the ability to accurately control a plasma process.

According to principles of the present invention, an optical emission spectrography system is provided for monitoring the condition of a plasma in a plasma vacuum processing chamber and having a housing connectable to the chamber such that emitted radiation from the chamber traverses a monitoring signal path from the plasma, into and through the housing, and out a window on the opposite side of the housing to a monitoring signal sensor that measures light from the spectrum emitted from the plasma. A separate reference signal path is provided that also passes through the housing from a reference source on one side to a reference signal sensor outside a separate window on the side of the housing opposite the reference source.

In certain embodiments of the invention, a processor receives the signals from both sensors and corrects a measurement of the signal emitted by the plasma with information from the reference signal sensor, to compensate for attenuation of the signals caused by deposits on the windows. The reference signal from the reference signal source is knowable, either from known source settings or preferably by providing a separate sensor at the source. From this knowledge, attenuation of the reference signal received by the reference signal sensor can be determined and appropriately attributable by the processor to the condition of the window through which the reference signal is measured.

According to embodiments of the present invention, the system is configured to ensure that the deposits onto the windows through which the plasma emission and reference signals pass are substantially the same. The processor can then use the determined attenuation of the reference signal to adjust the measured emission from the plasma to compensate for the attenuation due to coating on the window through which the monitored emission from the plasma passes.

In accordance with the illustrated embodiments of the invention, a set of baffles, wall structure and openings therein are provided within the housing to facilitate the randomization of material propagating from the chamber that can deposit onto the windows. The baffles are arranged in substantially identical configurations within substantially identical legs that radiate from a central cavity and lead to each of the respective windows. The legs contain separate line-of-sight paths for the monitoring and reference signals.

Potential deposits on the windows are impeded from flowing toward the windows by provision of counterflow flow of gas through a counterflow tube through which the emissions to be measured pass. The tube extends between the center of the central cavity to an isolation chamber located between the central part of the housing and the plasma chamber. Purge gas is fed into housing proximate the legs and flows through the counterflow tube to the isolation chamber, from which it is exhausted, preferably by a dedicated vacuum pump separate from those used to maintain vacuum in the processing chamber. Additional baffle surfaces along the monitoring signal and counterflow path collect coating material deposits, thereby removing them from the gas within the housing. These and other techniques that are known to limit the propagation of contaminating vapor in a vacuum system can be used in combination with the optical system configuration.

The optical system measurement of plasma emission can be used to monitor the process in the chamber and to facilitate the control of deposition, etch, chamber cleaning and other processes within the clamber. The optical system processor and the processing system controller can be coordinated or combined to accomplish such control.

These and other objects and advantages of the present invention will be more readily apparent from the following detailed description of illustrated embodiments of the invention.

BRIEF DESCRIPTION OF THE DRAWINGS

The FIGURE is a diagrammatic representation of a plasma processing apparatus having an optical emission spectroscopy system according to one embodiment of the present invention.

DETAILED DESCRIPTION

The FIGURE diagrammatically illustrates a plasma processing system 10 of the type used for processing semiconductors and other related substrates. The system 10 includes a vacuum chamber 12 in which is situated a substrate holder 14 on which may be mounted a semiconductor wafer 15 for processing. A plasma source is provided within the chamber 12 to energize a plasma 16 in process gas maintained under vacuum within the chamber 12. The plasma source can include a pair of electrodes, which can include the holder 14 and a sputtering target or other electrode 18, or can include some other plasma generating system, for example an inductively coupled plasma (ICP) source that typically includes an RF inductive or capacitive electrode coupled to the plasma from inside or outside of the chamber 12. A programmed controller 20 is typically provided to maintain reliable and repeatable operation of the apparatus 10 and to precisely control the process.

To monitor the condition of the plasma 16, and to provide the controller 20 with information for control of the plasma and the process performed with the plasma 16 in the chamber 12, a self-calibrating optical emission spectroscopy (OES) system 30 is provided. The system 30 is mounted to the outside of the chamber 12 and coupled to the inside of the chamber 12 through a gate valve 24. The valve 24 is situated to provide an observation path for the OES 30, preferably a straight line-of-sight path to the plasma 16, represented by arrows 31 and 32 in the FIGURE. The OES includes a plasma measurement device or optical sensor 35 that lies on the path 31-32. The sensor 35 is capable of receiving and measuring a spectrum of emitted radiation from the plasma 16, or at least a set of selected wavelengths of radiation within a spectrum, that preferably includes the wavelengths of visible light, or selected wavelengths of radiation in or outside of the spectrum of visible light, that contains the information of interest in monitoring the condition and properties of the plasma 16.

The OES system 30 is provided with housing 36 that isolates the vacuum interior thereof, which, during operation, is in communication with the vacuum within the chamber 12 through the gate valve 24, from the surrounding atmosphere in which the sensor 35 is situated. The sensor 35 is isolated from the plasma environment by a window 38 in a main branch or leg 39 of the housing 36. The window 38 lies in line with and perpendicular to the path 31-32. A central spherical cavity 40 is provided inside of and at the center of the housing 36 with its center lying on the path 31-32. A pair of holes 41 and 42 are provided in the wall of the cavity 40, on a diameter thereof that is in line with the path 31-32. Additionally, a series of baffles 43-46 are provided on the opposite sides of the cavity 40, each having a hole therein lying on the path 31-32.

A purge gas supply 50 is connected to a space 49 inside of the housing 36. The supply 50 may contain the same gas as the processing gas within the chamber 12, a neutral gas or other gas compatible with the process within the chamber. Usually, the active chemicals are a small part of the processing gas, with a neutral gas such as argon making up most of it. Typically a suitable purge gas would be helium or argon, or the same gas as the processing gas or a neutral gas that is a carrier gas component of the processing gas. The purge gas is supplied to the space 49 within housing 36 at a pressure that is at least slightly greater than that within the chamber 12 so that the purge gas propagates generally from the housing 36 toward the chamber 12, or at least to an isolation chamber 51 within the housing 36 to which an exhaust vacuum pump 52 is coupled through an exhaust shut-off valve 53. The isolation chamber 51 communicates with the chamber 12 through the hole in baffle 43 and through gate valve 24, so that process gas from chamber 12 is predominantly exhausted from the isolation chamber 51 through the exhaust pump 52 and a minimum amount of the process gas from the chamber 12, which contains the substances that would tend to coat and contaminate the window 38, are minimized.

The isolation chamber 51 is separated from the space 49 by the baffle 44, which is sealed to the wall of the housing 36 at its outer edges and to the wall of the cavity 40 around the edge of the hole in the baffle 44. In this way, purge gas from the supply 50 passes is injected into the space 49, propagates generally into the cavity 40 and from there into the isolation chamber 51. The propagation of gas into the cavity 40 from the space 49 within the housing 36 is through the hole 42 in the wall of cavity 40 and also through additional holes 47 and 48 in the wall of the cavity 40, which are provided taking reference measurements, as explained below.

The housing 36 is provided with side legs or branches 55 and 56. The insides of the branches 39, 55 and 56 are in communication with the space 49 into which the purge gas flows from the source 50. Leg 55 is a reference source leg while leg 56 is a reference sensor leg. A reference source 60 is provided adjacent the reference source leg 55, lying on a reference signal path represented by the arrows 61 and 62 that is perpendicular to the path 31-32 and intersects the path 31-32 at the center of the cavity 40. The reference source 60 emits a signal along the path 31-32, through a window 67 in the end of the leg 55 of the housing 36. The holes 47 and 48 in the wall of cavity 40 lie on path 61-62. A reference signal optical sensor 65 is provided adjacent the reference sensor leg 56 on the path 61-62. The sensor 65 is directed toward the reference source 60 to receive emissions from the reference source 60 along the path 61-62, and through a window 68 in the wall of the housing 36 at the end of the leg 56. A pair of baffles 71 and 72 are positioned in the reference source leg 55 of the housing 36. The baffles 71, 72 have holes at their centers that lie on the path 61-62. Similarly, a pair of baffles 73 and 74 are positioned in the reference sensor leg 56 of the housing 36. The baffles 73, 74 also have holes at their centers that lie on the path 61-62.

Additionally, a counterflow tube 75 is provided in alignment with the path 31-32. The interior of the tube 75 is lined with a series of baffles 76, each having a hole therein aligned on the path 31-32. The outside of the tube 75 is sealed to the edge of the opening 41 in the wall of the cavity 40 and to the edge of the hole in the baffle 44. The tube 75 has a gas inlet 77 near the center of the cavity 40 and a gas outlet 78 within the isolation chamber 51. The gas outlet is the inlet for radiation from the plasma that is being measured by the sensor 35 after it travels along path 31-32 through the tube 75 and out the gas inlet 77 thereof.

An optical calibration sensor 85 is provided adjacent the source 60 to adjust the emissions from the source 60 so that it essentially replicates at least a portion of the spectrum of the normal emission from the plasma 16 that is to be measured by the sensor 35. The sensors 35, 65 and 85 have outputs connected to a processor 80, which controls the source 60 and communicates with the controller 20 of the system 10.

In time and over the course of extended operation, the window 38 will experience a mild window coating, which can be enough to affect the measurements made by sensor 35 of the emissions from the plasma 16 that propagate along path 31-32. The coating is considered "mild" due to details of the system 30 that have been provided to reduce the rate of coating on all the windows 38, 67 and 78. These details help to ensure that the coatings are the same or similar on all the windows 38, 67 and 68. These details include the provision that all three legs 39, 55 and 56 with windows 38, 67 and 68, respectively, of the optical system 30 contain optical baffles, which are baffles 45 and 46 in leg 39, baffles 71 and 72 in leg 55 and baffles 73 and 74 in leg 56. These baffles function in conjunction with the respective holes 42, 47 and 48 in the wall of the cavity 40 to achieve these goals, which include reducing the flow of reactants to the windows 38, 67 and 68.

To impede the flow of process gases to the windows 38, 67 and 68, the inert purge gas, preferably the carrier gas used in the process chamber, is fed into the space 49 of the housing 36 of the optical system 30 with a two-fold goal: to create a flow of gas that will reduce the flow of reactants to the reference and diagnostic parts of the optical system 30, and to create a volume with many gas collisions that will tend to ensure that the reactant gas flow from the plasma 16 to all parts of the optical system 30 will be the same or similar.

The portion of the housing 36 that connects the optical system 30 to the process chamber 12 contains a baffle with the long slender counter-flow tube 75, preferably having a diameter of about ⅛ inch. In the counterflow tube 75, gas reactants will have to diffuse counter to the purge gas flow in order to reach the windows 38, 67 and 68. The role of the counterflow tube 75 is three-fold: to collimate the light to the detector along the path 31-32, to provide a large surface area on which the process reactants can deposit, and to define flow that will impede the reactants' diffusion to the rest of the optical system. Thus to enhance this deposition, the tube 75 can be heated. It can also be designed to have a large surface area, which is what the baffles 76 within it can provide.

In addition, the isolation chamber 51 provided between the baffle plates 43 and 44 in the portion of the housing 36 of the optical system 30 that is connected to the chamber 12 is evacuated by means of the pump 52. This is preferably a turbo-molecular pump. The role of this pump is to create a large pressure differential for gas flow along the tube 75.

To ensure that reactant gas to all the windows 38, 67 and 68 is the same, the inside of the housing 36 of the optical system 30 has to be designed with care. The central space includes a spherical shell that forms the wall of the spherical cavity 40. The shell has three gas inlet openings 42, 47 and 48 for optical access to the windows 38, 67 and 68, plus one gas outlet opening 41 for the counterflow tube 75. The counterflow tube 75 is located so that its inlet opening 77 is at the center of the spherical cavity 40. The spherical shape of the cavity 40, the small diameter of the counterflow tube 75, and the central location of its inlet opening 77 all facilitate keeping substantially identical the flux of potential coating material to the windows 38, 67 and 68.

Further, if after initial calibration tests, the film thickness on the windows is still not the same, compensation for unequal deposition rates on the windows can be made by adjusting the diameters of the holes in the baffles, preferably the baffles 71-74 in the reference legs 57 and 58.

The purge gas from source 50 is fed into the space 49 surrounding the spherical shell surrounding cavity 40. From there it flows into the cavity 40 through the three openings 41, 47 and 48. From the cavity 40, the gas flows through the counterflow tube 75 to the isolation chamber 51 from which it is exhausted by pump 52.

To further insure that all the windows have the same coating, the windows 38, 67 and 68 and the branches of the optical system 30 containing them, should be kept at the same uniform temperature. This can include providing heating pads and temperature control circuitry (not shown) around the optical system 30.

This invention depends on the light attenuation of all the windows to be the same or similar. After many hours of operation, the coating on the baffles becomes thick, and the coating may start to peel. This can result in the flakes falling on the windows. To prevent the flakes from falling onto the windows, the legs of the optical system containing the windows should be in the same horizontal plane.

In operation, before the plasma process in chamber 12 begins, the optical system 30 calibrates itself with the processor 80 causing the activation of the reference source 60. The spectrum emitted from the source 60 is set to approximately that expected to be received from the plasma 16. The output of the reference source 60 is sensed by the reference calibration sensor 85, which communicates the reference signal to the processor 80, which in turn compares the spectrum of the sensed signal to reference data stored at the processor 80 and readjusts a control signal to the source 60.

As a result, a reference signal is emitted from the source 60 along the path 61-62, through both windows 67 and 68, to the reference signal sensor 65 on the opposite side of the housing 36. The output of the sensor 65 is communicated to the processor 80, which interprets the received signal to determine the condition of the windows 67 and 68, from which it derives the condition of the window 38 through which the emissions from the plasma 16 are to be measured. The fact that the signal along path 61-62 passes through two windows, windows 67 and 68, is taken into account by the processor 80.

When the plasma 16 is ignited, a spectrum is emitted along the path 31-32 and received by the sensor 35 through the window 38. The sensor 35 then delivers a measurement signal to the processor 80, which compares the spectrum of the measurement signal with stored data to determine the condition of the plasma 16. In comparing the measurement signal, the processor corrects the measured signal based on the received reference signal from the sensor 65 in order to compensate for the derived condition of the window 38. The condition of the plasma 16, so determined, is communicated from the processor 80 to the controller 20 of the processing apparatus 10, which can control the operation of the apparatus 10 to adjust the plasma 16 or to take other action in response to the determined plasma condition.

Although only certain exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

What is claimed is:

1. A plasma monitor for a vacuum processing system, the monitor comprising:
    a vacuum tight housing connectable to a plasma processing chamber with an inside thereof in communication with a vacuum pressure environment within the chamber, the housing having at least two line-of-sight signal paths therethrough, including a monitoring signal path and a reference signal path;
    at least two windows in the housing, including a first window located in the monitoring signal path and a second window located in the reference signal path, each window having a side thereof in contact with the vacuum pressure environment and exposed to deposits thereon of film forming material from the vacuum pressure environment;
    a reference signal source located along the reference signal path;
    at least two optical sensors including a first sensor located outside of the first window in the monitoring signal path and a second sensor located outside of the second window in the reference signal path and oriented to receive and measure signals in the respective paths;
    the monitoring signal path extending from a plasma volume in the processing chamber when the housing is coupled thereto, through the housing and the first window, to the first sensor, and the reference signal path extending from the reference signal source, through the housing and the second window, to the second sensor;
    means including a central cavity within the housing at a point of intersection of the monitoring signal and reference signal paths for affecting the flow of the film forming material from the plasma volume and through the central cavity within the housing and equally along each of the monitoring signal and the reference signal paths to and onto the respective first and second windows so as to deposit film of the film forming material from the vacuum pressure environment substantially equally on the first and second windows; and
    a processor programmed to derive a measurement of emissions from the plasma volume in response to outputs from the first and second sensors.

2. The plasma monitor of claim 1 wherein:
    the means for affecting the flow of material includes a plurality of baffles arranged substantially identically along each of the reference signal and monitoring signal paths between the central cavity and the respective first and second windows to substantially equally affect the flow of film forming material to the respective first and second windows.

3. The plasma monitor of claim 1 wherein:
    the housing is configured in a plurality of effectively similar radially extending legs, including a first leg extending from the central cavity to the first window and surrounding a portion of the first path and a second leg extending from the central cavity to the second window and surrounding a portion of the second path.

4. The plasma monitor of claim 1 wherein:
    the means for affecting the flow of material includes a counterflow system including means for affecting a flow of gas from a portion of the housing containing the windows toward the processing chamber.

5. The plasma monitor of claim 1 wherein the means for affecting the flow of material includes:
    a plurality of legs, including a first leg extending radially from a central portion of the housing to the first window and surrounding a portion of the first path, and a second leg extending radially from the central portion of the housing to the second window and surrounding a portion of the second path; and
    a counterflow system including means for affecting a flow of gas from a portion of the housing containing the first and second legs to the central portion of the housing, and then from a central portion of the housing toward the processing chamber.

6. The plasma monitor of claim 1 wherein the means for affecting the flow of material includes:
    a first leg extending radially from a central portion of the housing to the first window and surrounding a portion of the first path, and a second leg extending radially from the central portion of the housing to the second window and surrounding a portion of the second path;
    a purge gas supply connected to the housing near the first and second legs;
    an exhaust volume in the housing between the central portion thereof and the processing chamber, the exhaust volume having an exhaust pump connected thereto; and
    a counterflow tube extending from the central portion of the housing to the exhaust volume, the tube being concentric with and surrounding a portion of the first path between the central portion and the exhaust volume.

7. A vacuum processing apparatus comprising the plasma monitor of claim 1.

8. A plasma monitor for a vacuum processing system, the monitor comprising:
    a vacuum tight housing connectable to a plasma processing chamber and enclosing a vacuum pressure environment exposed to film forming material from the plasma processing chamber, the housing having at least two line-of sight signal paths passing through the vacuum pressuring environment within the housing, the paths including a monitoring signal path and a reference signal path;

at least two windows in the housing, including a first window located in the monitoring signal path and a second window located in the reference signal path, the first and second windows intersecting the respective monitoring and reference signal paths at substantially the same angles, each window having a side thereof in contact with the vacuum pressure environment within the housing;

a reference signal source;

at least two optical sensors including a first sensor located outside of the first window in the monitoring signal path and a second sensor located outside of the second window in the reference signal path and oriented to receive and measure signals in the respective paths;

the monitoring signal path extending from a plasma volume in the processing chamber when the housing is coupled thereto, through the housing and the first window, to the first sensor, and the reference signal path extending from the reference signal source, through the housing and the second window, to the second sensor;

a processor responsive to outputs from the first and second sensors and programmed to derive a measurement of emissions from the plasma volume by processing output from the first sensor in accordance with output of the second sensor;

a central cavity centered on a point of intersection of the first and second paths;

the housing including a first leg extending from the central cavity to the first window and surrounding a portion of the first path and a second leg, substantially identical to the first leg, extending from the central cavity to the second window and surrounding a portion of the second path, each leg having substantially equal dimensions, and each including an equal plurality of baffles substantially equally configured and arranged along each path to substantially equally affect the flow of film forming material to the respective first and second windows;

a purge gas supply connected to the housing near the first and second legs;

an exhaust volume in the housing between the central cavity and the processing chamber, the exhaust volume having an exhaust pump connected thereto; and a counterflow tube extending from the central cavity to the exhaust volume, the tube being concentric with and surrounding a portion of the first path between the central cavity and the exhaust volume.

9. The plasma monitor of claim 8 wherein:

the at least two windows in the housing includes a third window located in the reference signal path between the central cavity and the reference signal source;

the plurality of radially extending legs includes a third leg extending from the central cavity to the third window and surrounding a portion of the second path.

10. A vacuum processing apparatus comprising the plasma monitor of claim 8.

11. A vacuum processing apparatus comprising a processing chamber, the plasma monitor of claim 8 and a controller programmed to control plasma parameters within the processing chamber in response to a plasma emissions measurement signal from the plasma monitor.

12. A semiconductor wafer processing apparatus comprising:

a vacuum processor including a plasma processing chamber having a plasma volume therein;

a plasma energy source coupled to the plasma volume;

a substrate support in the chamber facing the plasma volume;

a plasma monitor having a vacuum tight housing connected to a plasma processing chamber and enclosing a vacuum pressure environment exposed to film forming material from the plasma processing chamber, the housing having at least two line-of-sight signal paths passing through the vacuum pressuring environment within the housing, the paths including a monitoring signal path and a reference signal path, the plasma monitor further including:

at least two windows in the housing, including a first window located in and perpendicular to the monitoring signal path and a second window located in and perpendicular to the reference signal path, each window having a side thereof in contact with the vacuum pressure environment within the housing;

a reference signal source;

at least two optical sensors including a first sensor located outside of the window in the monitoring signal path and a second sensor located outside of the window in the reference signal path and oriented to receive and measure signals in the respective paths;

the monitoring signal path extending from the processing chamber, through the housing and the first window, to the first sensor, and the reference signal path extending from the reference signal source, through the housing and the second window, to the second sensor;

a central cavity centered on a point of intersection of the first and second paths;

an equal plurality of baffles along each of the reference signal and monitoring signal paths and substantially equally configured between the central cavity and the respective first and second windows to substantially equally affect the flow of film forming material to the respective first and second windows;

the housing including a first leg extending from the central cavity to the first window and surrounding a portion of the first path and a second leg, substantially identical to the first leg, extending from the central cavity to the second window and surrounding a portion of the second path, each leg having substantially equal dimensions;

a purge gas supply connected to the housing near the first and second legs;

an exhaust volume in the housing between the central cavity and the processing chamber, the exhaust volume having an exhaust pump connected thereto; and a counterflow tube extending from the central cavity to the exhaust volume, the tube being concentric with and surrounding a portion of the first path between the central cavity and the exhaust volume;

the at least two windows in the housing including a third window located in the reference signal path between the central cavity and the reference signal source;

the plurality of radially extending legs including a third leg extending from the central cavity to the third window and surrounding a portion of the second path; and a control system programmed to derive a measurement of emissions from the plasma volume in response to the output from the first sensor in accordance with the output of the second sensor and to control a plasma within the plasma processing chamber in response to the measurement.

* * * * *

UNITED STATES PATENT AND TRADEMARK OFFICE
CERTIFICATE OF CORRECTION

PATENT NO.       : 7,537,671 B2                                       Page 1 of 1
APPLICATION NO.  : 11/536976
DATED            : May 26, 2009
INVENTOR(S)      : Vukovic It is certified that error appears in the above-identified patent and that said Letters Patent is hereby corrected as shown below:

On the title page:
In the Abstract, lines 1-2, "monitor therefor is provided" should read --monitor therefor are provided--.

In Column 2, line 9, "is disclosed." should read --are disclosed.--.

In Column 2, line 18, "In addition to the monitoring" should read --In addition to monitoring--.

In Column 4, line 65, "supply 50 passes is injected" should read --supply 50 is injected--.

Signed and Sealed this
First Day of May, 2012

David J. Kappos
*Director of the United States Patent and Trademark Office*